US007749210B2

(12) United States Patent
Mishima et al.

(10) Patent No.: US 7,749,210 B2
(45) Date of Patent: *Jul. 6, 2010

(54) DISPOSABLE DIAPER (75) Inventors: Yoshitaka Mishima, Kagawa-ken (JP);
Hironao Minato, Kagawa-ken (JP);
Nariaki Shimoe, Kagawa-ken (JP)

(73) Assignee: Uni-Charm Corporation,
Shikokuchuo-shi, Ehime-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/944,323

(22) Filed: Nov. 21, 2007

(65) Prior Publication Data

US 2008/0077110 A1 Mar. 27, 2008

Related U.S. Application Data (62) Division of application No. 10/944,408, filed on Sep. 20, 2004, now Pat. No. 7,326,192.

(30) Foreign Application Priority Data

Jul. 30, 2004 (JP) .............................. 2004-224724

(51) Int. Cl.
*A61F 13/15* (2006.01)
(52) U.S. Cl. .............................. 604/385.24; 604/385.26; 604/385.27; 604/385.28; 604/385.21; 604/385.19
(58) Field of Classification Search ............. 604/385.19, 604/385.24, 385.26, 385.27, 385.28, 385.21
See application file for complete search history.

(56) References Cited

U.S. PATENT DOCUMENTS

| 5,718,698 A * | 2/1998 | Dobrin et al. ............... 604/383 |
| 7,326,192 B2 * | 2/2008 | Mishima et al. ........ 604/385.19 |

FOREIGN PATENT DOCUMENTS

| JP | 03-218751 | 9/1991 |
| JP | 04-150853 | 5/1992 |
| JP | 04-322646 | 11/1992 |
| JP | 4-322646 A | 11/1992 |
| WO | 99/08640 | 2/1999 |
| WO | 99/16398 | 4/1999 |
| WO | 99/16398 A1 | 4/1999 |
| WO | 03/000975 A1 | 2/2003 |
| WO | 03/009795 | 2/2003 |

OTHER PUBLICATIONS

European Search Report of International Application No. 05767243. 8-2124 / 1774937 PCT/JP2005013959 mailed Jul. 13, 2009.

* cited by examiner

*Primary Examiner*—Jacqueline F. Stephens
(74) *Attorney, Agent, or Firm*—Lowe Hauptman Ham & Berner, LLP (57) ABSTRACT A disposable diaper has a through-hole formed in an inner sheet destined to come in contact with a wearer's skin so that this through-hole may communicate with a pocket for receiving feces. The inner sheet is formed with an elastic area extending in a longitudinal direction along transversely opposite side edges of the through-hole. In a crotch region of the diaper, a stiffening sheet strips are attached to the inner sheet between the transversely opposite side edges of the diaper and the transversely opposite side edges so that the respective stiffening sheet strips extend in a transverse direction.

21 Claims, 5 Drawing Sheets

DISPOSABLE DIAPER

RELATED APPLICATIONS

The present application is based on, and claims priority from, Japan Application Number 2004-224724, filed Jul. 30, 2004 and U.S. patent application Ser. No. 10/944,408, filed Sep. 20, 2004, the disclosure of which are hereby incorporated by reference herein in their entirety.

BACKGROUND OF THE INVENTION

The present invention relates to disposable diapers having a means adapted for receiving feces.

There has already been proposed disposable diapers having a pocket as a means adapted for receiving feces, comprising a first sheet facing a wearer's skin and a second sheet facing the wearer's garment wherein, in a crotch region of the diaper, the first sheet is formed with a through-hole communicating with the feces receiving pocket defined between the first and second sheets so that the through-hole may be aligned with anus of the wearer when the diaper is put on the wearer's body.

For example, U.S. Pat. No. 4,990,147 (Citation 1) discloses a disposable diaper comprising a liquid-impervious backsheet, a liquid-pervious liner and a bodily waste absorbent core interposed between the backsheet and the liner. The liner is formed with a through-hole adapted to guide feces therethrough toward the core and thereby to protect the wearer's skin from being contaminated with feces. The liner is formed at least partially by an elastic panel serving to keep a periphery of the through-hole in close contact with an area surrounding the anus. In this diaper, a stock material for the elastic panel may be selected from the group consisting of a nonwoven fabric of a polyurethane elastic threads and a knitted fabric of inelastic threads.

Figure 8:
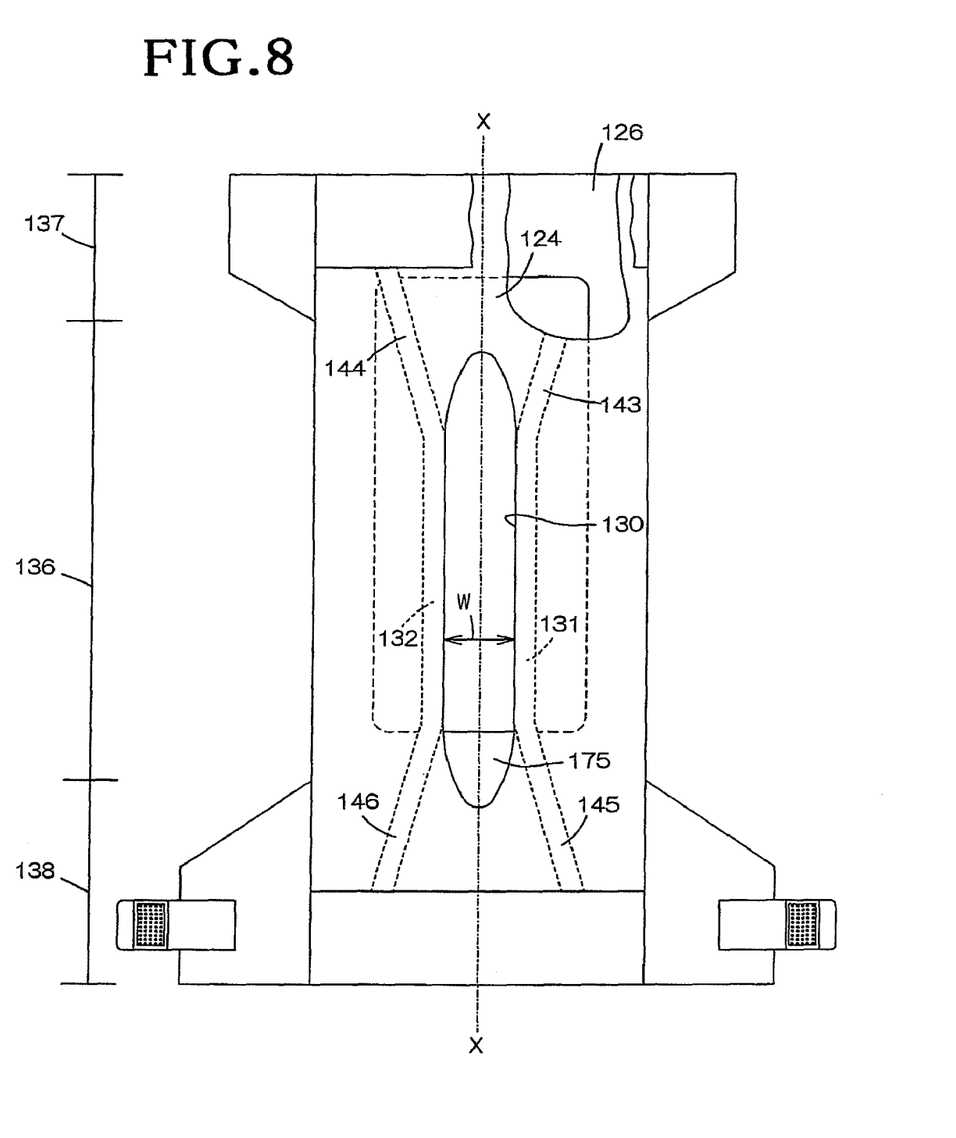
FIG. 8 is a partially cutaway plan view showing the diaper of prior art as its elastically stretched state.
Figure 9:
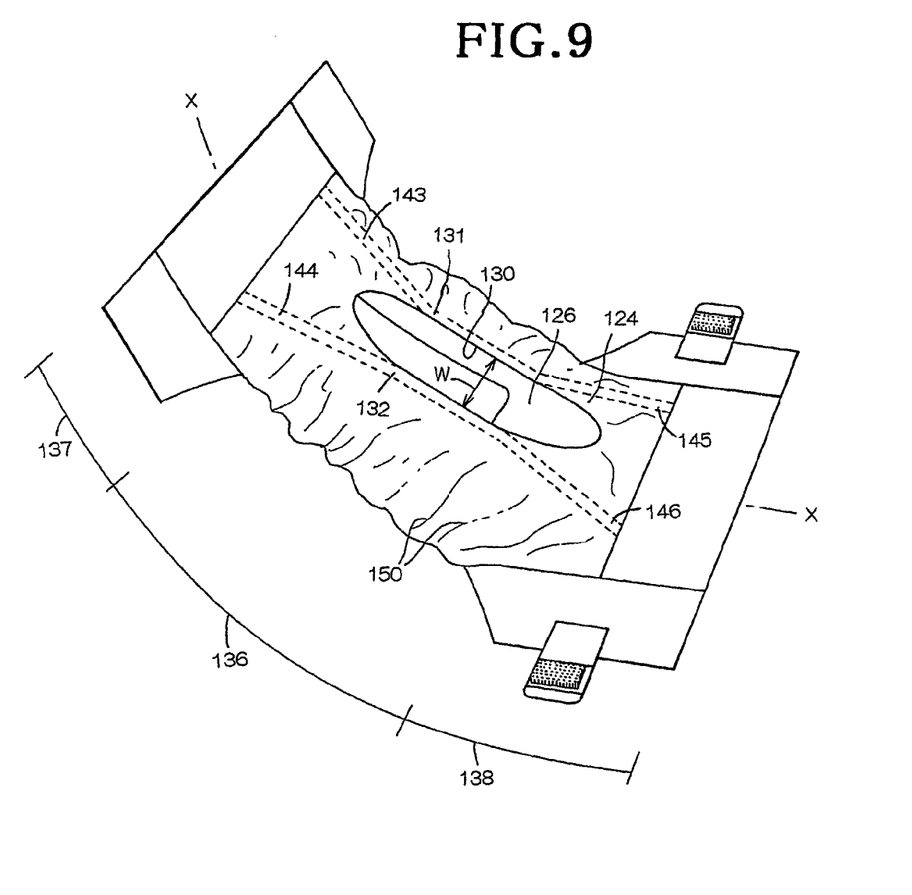
FIG. 9 is a perspective view showing the diaper of FIG. 8 in its elastically contracted state.

WO 03/009795 A1 (Citation 2) discloses a disposable diaper as illustrated in FIGS. 8 and 9 of the accompanying drawings wherein FIG. 8 illustrates the diaper in its elastically stretched state and FIG. 9 illustrates the diaper in its elastically contracted state. The known disposable diaper comprises a backsheet 126 and a topsheet 124 formed with a slit-type opening 130 allowing feces to pass therethrough so that a pocket serving for receiving feces may be defined between the top- and backsheets 124, 126. Along a pair of transversely opposite side edges of the slit-type opening 130, elastic bands are bonded in stretched states to the topsheet 124 so as to form elastic areas 131, 132 extending in parallel with the center line X in a longitudinal direction. The elastic area 131 is contiguous to an elastic area 143 obliquely extending toward a front waist region so as to draw apart gradually from the center line X, on one hand, and to an elastic area 145 obliquely extending toward a rear waist region so as to draw apart from the center line X, on the other hand. In the similar manner, the elastic area 132 is contiguous to an elastic area 144 obliquely extending toward the front waist region so as to draw apart gradually from the center line X, on one hand, and to an elastic area 146 obliquely extending toward a rear waist region so as to draw apart gradually from the center line X, on the other hand. The elastic areas 131, 143, 145 cooperate with the elastic areas 132, 144, 146 opposed to the areas 131, 143, 145 to define a generally X-shaped elastic zone. The slit-type opening 130 may be positioned in alignment with the anus when the known diaper is put on the wearer's body.

The liner of the diaper disclosed in Citation 1 as well as the topsheet of the diaper disclosed in Citation 2 may be formed from the elastic sheet. One example of such elastic sheet is a nonwoven fabric of elastic threads such as polyurethane elastic threads, which falls, however, into disfavor with wearer's mothers due to uncomfortable rubber-like touch peculiar to this nonwoven fabric. The other example of such elastic sheet is knitted fabric of inelastic threads, which is, however, too costly to be used for the disposable diaper. For the diaper disclosed in Citation 2, the elastic threads may be attached to the nonwoven fabric of inelastic threads to ensure that this nonwoven fabric is partially elasticized. The topsheet formed from a nonwoven fabric made of inelastic threads and partially elasticized in this manner certainly solves the problem that the wearer might experience uncomfortable rubber-like touch so far as the diaper is in the state as shown in FIG. 8. However, in response to elastic contract of the elastic bands, a width W of the slit-type opening is varied and simultaneously the crotch region is formed with a plurality of irregular and outstanding corrugations 150. Variation occurring in the width W of the slit-type opening makes it difficult to position the side edges of the slit-type opening in alignment with the both lateral sides of the wearer's anus. Such unstable width of the opening must be alleviated by minimizing the width W of the opening and covering the wearer's skin with the topsheet in the vicinity of the diaper wearer's anus so that the wearer's skin may be protected from being contaminated over a wide range. Formation of a plurality of corrugations prevents the topsheet from being kept in close contact with the wearer's skin, resulting in that bodily waste may leak out beyond the periphery of the slit-type opening and/or appearance of the diaper put on the wearer's body may be damaged. It is a principal object of the present invention to improve the disposable diaper of prior art so that the problems as have been described just above may be reliably solved.

SUMMARY OF THE INVENTION

The present invention is directed to a disposable diaper comprising a chassis having a crotch region, a front waist region extending forward from the crotch region and a rear waist region extending rearward from the crotch region, and a liquid-absorbent panel interposed between a first sheet defining an inner surface of the chassis and facing a wearer's skin and a second sheet defining an outer surface of the chassis and facing the wearer' clothes. The first sheet being spaced, in a transversely middle zone of the crotch region, from the second sheet as well as from the body fluid absorbent panel in a thickness direction of the first sheet to define a pocket adapted to receive feces, the first sheet being formed along a center line bisecting a width of the crotch region with a through-hole extending in a longitudinal direction toward the front waist region and the rear waist region, respectively, in communication with the pocket, the through-hole being provided along its transversely opposite side edges extending in parallel to each other on both sides of the center line with elastic members attached in stretched states to the first sheet. The elastic members respectively comprise intermediate sections extending in the longitudinal direction along the transversely opposite side edges of the through-hole and sections extending from the intermediate sections so as to be gradually spaced away from the center line.

The diaper according to the invention further comprises the first sheet in the crotch region being formed between the transversely opposite side edges of the diaper extending in the longitudinal direction and the transversely opposite side edges of the through-hole with a means adapted for locally enhancing a flexural stiffness of the first sheet in the transverse direction of the diaper so as to restrict a deformation of the first sheet in the transverse direction.

According to one preferred embodiment of the invention, the restricting means are formed intermittently in the longitudinal direction.

According to another preferred embodiment of the invention, the restricting means are formed from bonding sheet strips prepared separately of the first sheet to the first sheet.

According to still another preferred embodiment of the invention, the restricting means are formed by coating the first sheet with hot melt adhesive.

According to still another preferred embodiment of the invention, the first sheet comprises a nonwoven fabric of thermoplastic synthetic fibers and the restricting means comprise film-like spots formed by locally melting and solidifying the nonwoven fabric.

According to further another preferred embodiment of the invention, the restricting means comprise corrugations of the first sheet regularly undulating in the longitudinal direction.

The first sheet has a flexural stiffness in the transverse direction of the diaper locally enhanced to define means adapted to restrain a deformation of the first sheet in the transverse direction of the diaper. This unique arrangement is effective to prevent the first sheet in the crotch region from significantly shifting in the transverse direction of the diaper and thereby to prevent the width between the side edges from being significantly varied even under elastic contraction of the elastic members extending in parallel to the center line along the side edges of the opening formed in the crotch region of the first sheet and then obliquely extending toward the front and rear waist regions so as to draw apart gradually from the center line.

The means adapted to restrain a significant deformation of the first sheet include bonding of sheet strips prepared separately of the first sheet to the first sheet intermittently in the longitudinal direction, forming the first sheet with a plurality of hot melt adhesive coated areas intermittently in the longitudinal direction of the diaper wherein each of these areas extends in the transverse direction of the diaper, forming film-like spots prepared by melting and solidifying the nonwoven fabric, and forming the first sheet with a plurality of gathers undulating in the longitudinal direction of the diaper.

PREFERRED EMBODIMENTS OF THE INVENTION

Details of a disposable diaper according to the present invention will be more fully understood from the description given hereunder with reference to the accompanying drawings.

Figure 1:
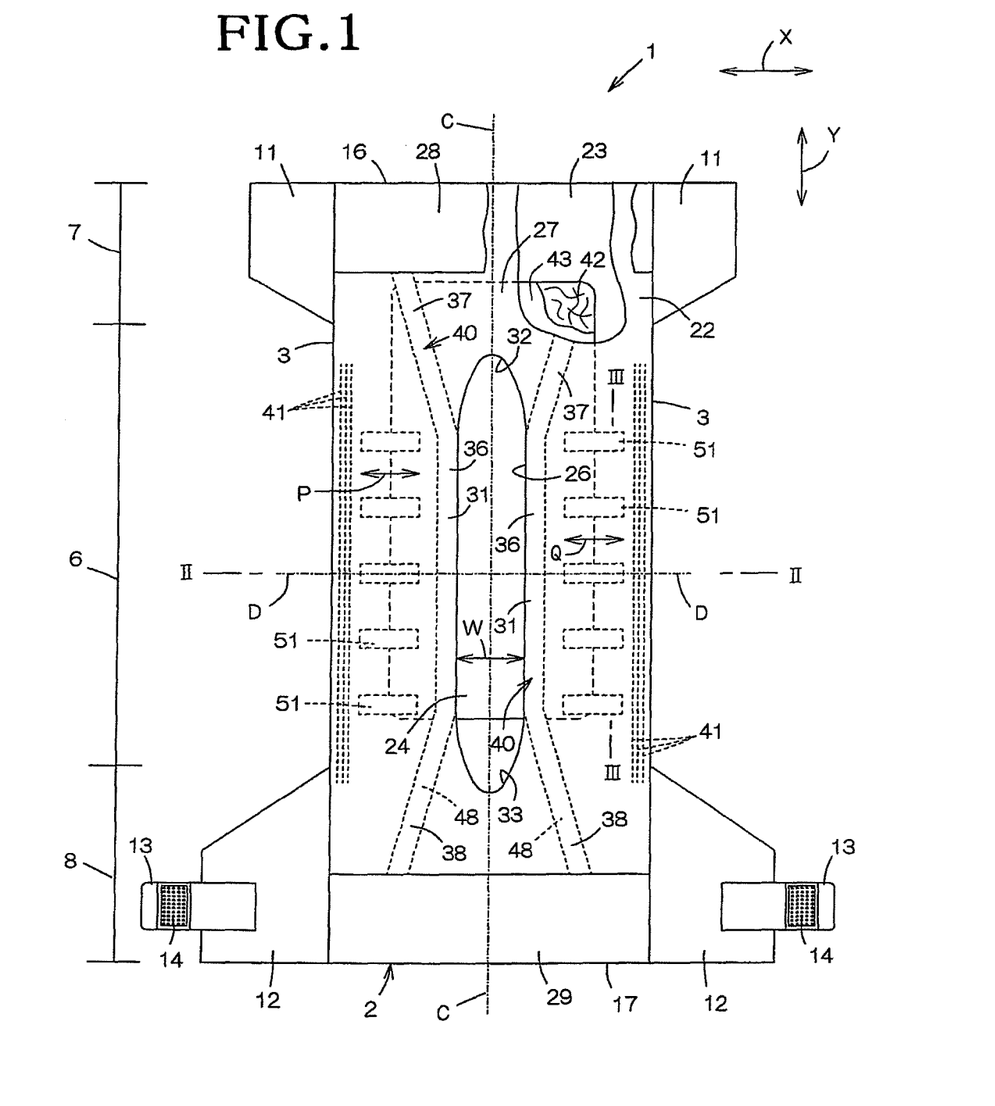
FIG. 1 is a partially cutaway plan view showing the disposable diaper according to a typical embodiment of the present invention in its elastically stretched state.

FIG. 1 is a partially cutaway plan view showing the disposable diaper 1 according to a typical embodiment of the present invention. The diaper 1 is illustrated herein as has been elastically stretched in a longitudinal direction Y corresponding to a vertical direction as viewed in FIG. 1 as well as in a transverse direction X. As viewed in the longitudinal direction Y, the diaper 1 has a crotch region 6 lying in a middle zone, a front waist region 7 extending forward from the crotch region 6 and a rear waist region 8 extending rearward from the crotch region 6. The diaper 1 further includes a chassis 2 which is rectangular in FIG. 1 and provided with a pair of front wings 11 respectively extending outward from transversely opposite side edges 3 of the chassis 2 in the front waist region 7 and a pair of rear wings 12 respectively extending outward from the transversely opposite side edges 3 in the rear waist region 8. The rear wings 12 are provided with tape fasteners 13 which are, in turn, formed on respective inner surfaces with pressure-sensitive adhesive areas 14.

The chassis 2 is contoured by the transversely opposite side edges 3 extending in the longitudinal direction Y of the diaper 1, and front and rear ends 16, 17 extending in the transverse direction X corresponding to a width direction of the diaper 1. The chassis 2 has an inner sheet 22 to contact with a wearer's skin and an outer sheet 23 to contact with the wearer's garment. The inner sheet 22 is formed with an oblong through-hole 26 extending in the longitudinal direction Y on the center line C-C bisecting a width of the diaper 1 so that a bodily waste absorbent panel 24 interposed between the inner and outer sheets 22, 23 may be seen through this through-hole 26. A periphery of the through-hole 26 is defined by a pair of transversely opposite side edges 31 extending in the longitudinal direction Y generally in parallel to the center line C-C, a front edge 36 generally describing a V-shape and a rear edge 33 generally describing an inverted V-shape. Front and rear bands 28, 29 both extending in the transverse direction X are attached to a surface of the inner sheet 22 facing the wearer's skin along the front and rear ends 16, 17, respectively. The inner sheet 22 further includes elastic areas 40 comprising intermediate sub-areas 36 extending along the transversely opposite side edges 31 of the through-hole 26 generally in parallel to the center line C-C, front sub-areas 37 obliquely extending from the vicinity of the front edge 32 of the through-hole 26 toward the front band 28 so as to draw apart gradually from the center line C-C and rear sub-areas 38 obliquely extending from the vicinity of the rear edge 33 of the through-hole 26 toward the rear band 29 so as to draw apart gradually from the center line C-C.

Figure 2:
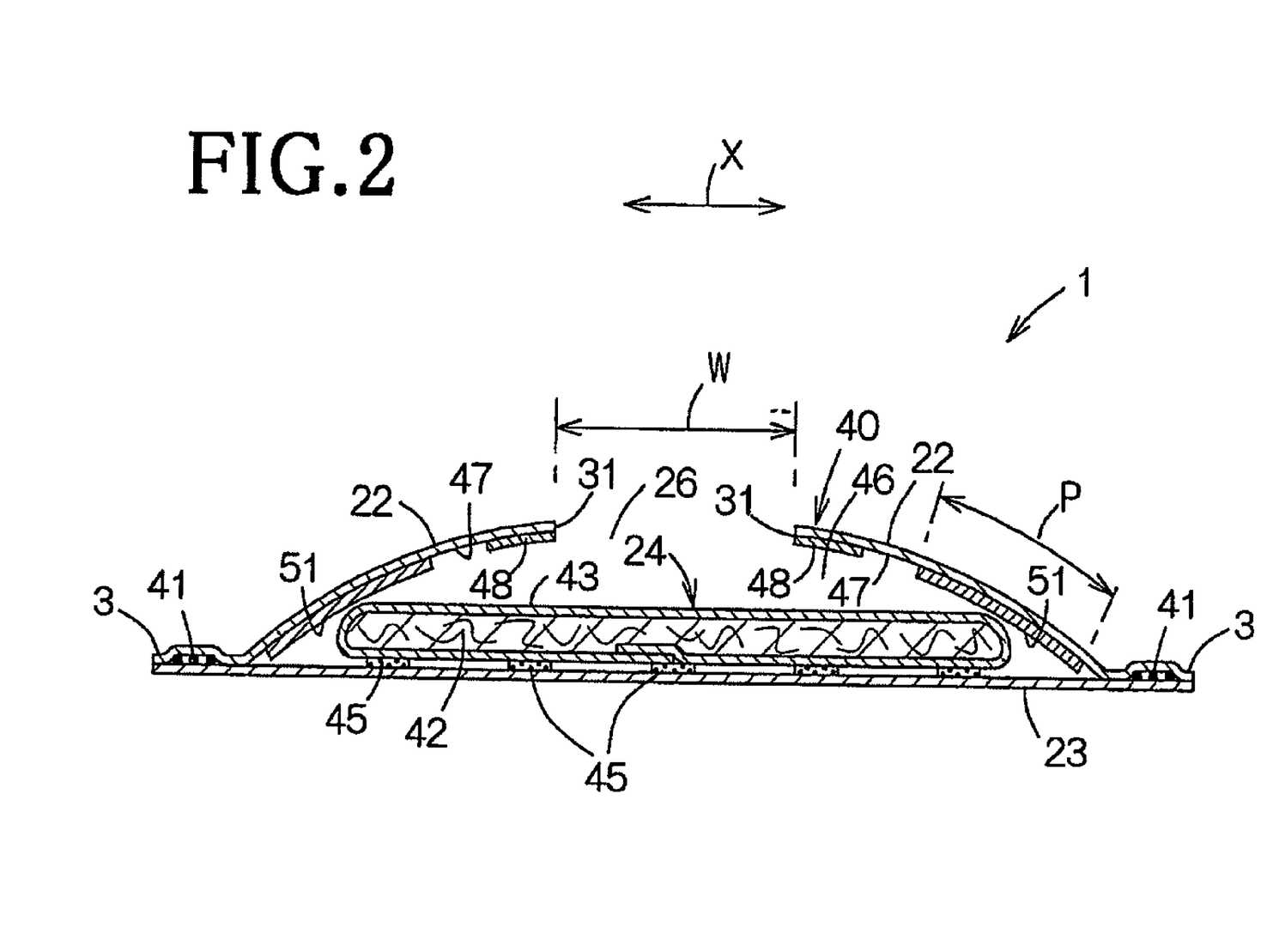
FIG. 2 is a sectional view taken along the line II-II in FIG. 1.

FIG. 2 is a sectional view taken along the line II-II corresponding to the center line D-D bisecting a dimension of the diaper 1 in the longitudinal direction Y. The inner and outer sheets 22, 23 are put flat and attached together using an adhesive means or a welding means along the transversely opposite side edges 3 as well as along the front and rear ends 16, 17 (See FIG. 1). Along the transversely opposite side edges 3, leg-surrounding elastic members 41 are interposed between the inner and outer sheets 22, 23 and bonded in stretched states to at least one of these sheets 22, 23 by means of hot melt adhesive (not shown) so as to extend in the longitudinal direction Y. The bodily waste absorbent panel 24 interposed between the inner and outer sheets 22, 23 comprises a core 42 formed from a mixture of fluff pulp and super-absorbent polymer particles or of fluff pulp and super-absorbent polymer fibers, in any case, wrapped with a sheet 43 such as a tissue paper and/or a nonwoven fabric. The bodily waste absorbent panel 24 is bonded to the outer sheet 23 by means of hot melt adhesive 45 (See FIG. 2). The inner sheet 22 is left free from the outer sheet 23 and the bodily waste absorbent panel 24 except the side edges 3 and the front and rear ends 16, 17 along which the inner sheet 22 is attached to the outer sheet 23 so that a pocket 46 adapted for receiving of feces may be formed between the inner and outer sheets 22, 23. The through-hole 26 of the inner sheet 22 is in communication with this pocket 46 and adapted to guide feces and/or urine into the pocket 46. In the vicinity of the transversely opposite side edges 31 of the through-hole 26, elastic bands 48 are bonded in stretched states to a surface 47 of the inner sheet 22 facing away from the wearer's skin by means of hot melt adhesive (not shown) so as to form the elastic areas 40. Furthermore, a plurality of stiffening sheet strips 51 (See FIG. 1) each extending in the transverse direction between each of the elastic area 40 and each of the side edges 3 are attached to the surface 47 facing away from the wearer's skin using an adhesive or a welding means. These stiffening sheet strips 51 locally enhance stiffness of the inner sheet 22 to alleviate a tendency that the inner sheet 22 might be formed with gathers as the elastic areas 40 are stretched and contracted in the longitudinal direction Y and thereby prevent the width of the inner sheet 22 as defined between the respective side edges 3 of the diaper 1 in the crotch region 6 and the respective side edges 31 of the through-hole 26 from being reduced in a direction indicated by an arrow P due to formation of the gathers. In other words, the width W between the side edges 31, 31 of the through-opening 26 is not significantly varied even when each of the elastic areas 40 is stretched and contracted and, therefore, the width W is maintained substantially constant before and after the diaper 1 is put on the wearer's body. In this way, both of the side edges 31 can be reliably positioned in the vicinity of the anus as the diaper 1 is put on the wearer's body. Since the stiffening sheet strips 51 are attached to the inner sheet 22 in the crotch region 6 so as to be arranged intermittently in the longitudinal direction Y and do not prevent the elastic areas 40 from contracting in the longitudinal direction, the stiffening sheet strips 51 allow the inner sheet 22 to be formed between each pair of the adjacent stiffening sheet strips 51 with a plurality of gathers which are relatively long in the transverse direction X and repetitively undulating in the longitudinal direction. In the crotch region 6 of such diaper 1 the gathers tend to be arranged in an orderly way in the crotch region 6 and present a good appearance when the diaper 1 is put on the wearer's body.

Of the diaper 1 constructed as has been described above, the inner sheet 22 is formed from a liquid-pervious inelastic nonwoven fabric, a woven fabric, a plastic film or the like. The outer sheet 23 is formed from a liquid-impervious, more preferably, liquid-impervious but breathable woven fabric, a nonwoven fabric, a plastic film or the like. The elastic bands 48 may be of natural or synthetic rubber and have widths in a range of 2 to 20 mm. The front and rear bands 28, 29 are optionally used to prevent the front and rear waist regions 7, 8 from being contracted in the transverse direction under the effect of the stretched elastic bands 48. These front and rear bands 28, 29 may be formed from a nonwoven fabric having a basis weight in a range of 30 to 400 g/m$^2$, a flexible and elastic foamed plastic sheet or the like. The through-hole 26 of the inner sheet 22 has a preferable dimensions, depending on the size of the diaper, to have the widths W ranging from 10 to 70 mm and a length sufficient to cover the anus and the urethral of the wearer.

Figure 3:
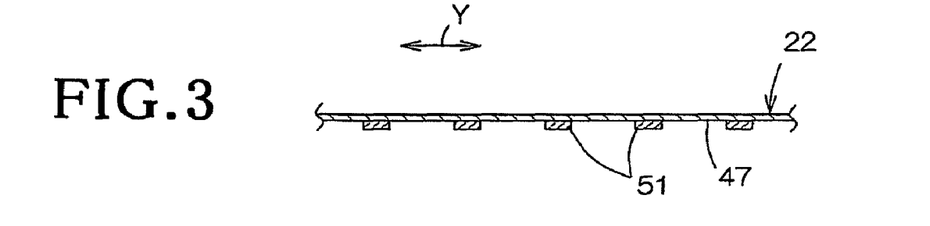
FIG. 3 is a sectional view of an inner sheet taken along the line III-III in FIG. 1.

FIG. 3 is a sectional view of an inner sheet 22 taken along the line III-III in FIG. 1. Each of the stiffening sheet strips 51 attached to the surface 47 of the inner sheet 22 facing away from the wearer's skin may be formed from a woven fabric, a nonwoven fabric, a plastic film, a flexible and elastic foamed plastic sheet or the like having a dimension in the transverse direction X of the diaper 1 less than a distance from the associated side edge 3 to the associated elastic band 48 (see FIG. 1) and dimensions in the longitudinal direction Y in a range of 2 to 20 mm. A distance between each pair of the adjacent stiffening sheet strips 51 is preferably in a range of 2 to 50 mm.

Figure 4:
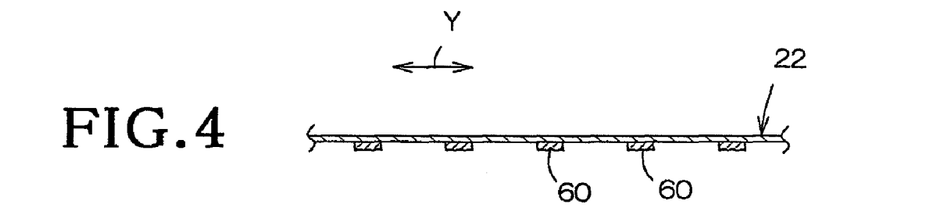
FIG. 4 is a view similar to FIG. 3, showing one preferred embodiment of the invention.
Figure 5:
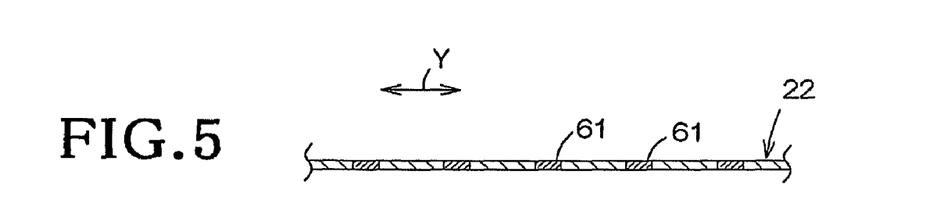
FIG. 5 is a view similar to FIG. 3, showing another preferred embodiment of the invention.
Figure 6:
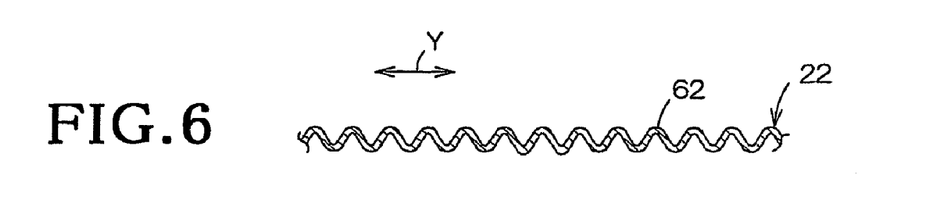
FIG. 6 is a view similar to FIG. 3, showing still another preferred embodiment of the invention.
Figure 7:
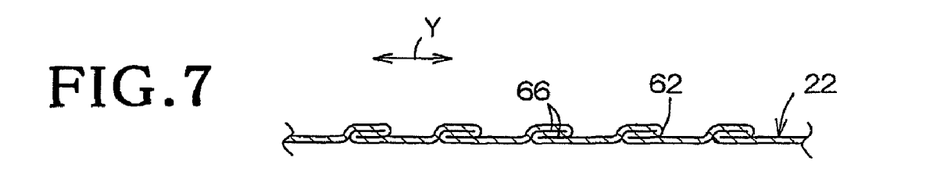
FIG. 7 is a view similar to FIG. 3, showing further another preferred embodiment of the invention.

FIG. 4 is a view similar to FIG. 3, showing preferred embodiments of the invention. In the case illustrated in FIG. 4, the stiffening sheet strips 51 are replaced by strips of hot melt adhesive 60 coated on the inner sheet 22 so as to extend in the transverse direction X. In the case illustrated in FIG. 5, the stiffening sheet strips 51 are replaced by film-like areas 61 formed intermittently in the longitudinal direction by locally melting and solidifying the inner sheet 22 made of the nonwoven fabric of thermoplastic synthetic fibers. These film-like areas 61 extend in the transverse direction X of the diaper 1 as in the case of the stiffening sheet strips 51 and have a stiffness higher than a stiffness of the nonwoven fabric left not melted to the film-like condition between each pair of the adjacent film-like areas 61. In the case illustrated by FIG. 6, the inner sheet 22 is formed with a plurality of gathers 62 regularly undulating in the longitudinal direction Y. Crests and troughs of these gathers 62 provide a function similar to those provided by the stiffening sheet strips 51 and the film-like areas 61. Finally in the case illustrated by FIG. 7, the inner sheet 22 is formed with a plurality of gathers 62 which are then collapsed so that the inner sheet 22 is bonded to itself using an adhesive means or a welding means in areas 66 in which the inner sheet 22 is placed upon itself.

The present invention allows the disposable diaper having the pocket for receiving feces to be improved so that the width of the through-opening communicating with the pocket can be substantially maintained constant even when the elastic members attached to the inner sheet of the diaper in stretched states are left to contract.

What is claimed is:
1. A disposable diaper, comprising:
    a chassis having a crotch region, a front waist region extending in a longitudinal direction of said diaper forward from said crotch region and a rear waist region extending in the longitudinal direction rearward from said crotch region;
    a liquid-absorbent panel interposed between a first sheet and a second sheet;
    said first sheet defining an inner surface of said chassis adapted to face a wearer's skin in use;
    the second sheet defining an outer surface of said chassis adapted to face away from said wearer' skin in use;
    said first sheet being spaced, in a transversely middle zone of said crotch region, from said body fluid absorbent panel in a thickness direction of said first sheet to define between said first sheet and said absorbent panel a pocket adapted to receive feces;
    said first sheet being formed along a center line bisecting a width of said crotch region with a through-hole that extends in the longitudinal direction toward said front waist region and said rear waist region, respectively, and is in communication with said pocket;

said through-hole being provided along transversely opposite side edges thereof with elastic members attached in stretched state to said first sheet, wherein each of said elastic members comprises
an intermediate section extending in said longitudinal direction along one of said transversely opposite side edges of said through-hole, and
two opposite end sections extending from said intermediate section towards said front and rear waist regions, respectively, while gradually diverging from said center line; and said first sheet in said crotch region being formed, between transversely opposite side edges of said diaper and said transversely opposite side edges of said through-hole, with a plurality of first and second zones arranged alternatingly in the longitudinal direction, wherein a flexural stiffness of said first sheet in a transverse direction of the diaper in said first zones is higher than in the second zones;

wherein each of said first zones is elongated in the transverse direction and has opposite inner and outer ends, the inner end being closer to the center line than the outer end.

2. The disposable diaper according to claim 1, wherein the inner end of each of said first zones is outwardly spaced in the transverse direction from the intermediate section of the elastic member that is closest to said first zone.

3. The disposable diaper according to claim 1, further comprising sheet strips elongated in the transverse direction and bonded to said first sheet in the first zones, said sheet strips increasing the flexural stiffness of said first sheet in the transverse direction in said first zones compared to said second zones in which said sheet strips are not present.

4. The disposable diaper according to claim 3, wherein said sheet strips are of a material different from that of said first sheet.

5. The disposable diaper according to claim 3, wherein
said first sheet comprises opposite inner and outer surfaces, the inner surface facing the absorbent panel and the outer surface facing away from the absorbent panel; and
said strips are directly bonded to the inner surface of said first sheet.

6. The disposable diaper according to claim 1, wherein
said first sheet comprises opposite inner and outer surfaces, the inner surface facing the absorbent panel and the outer surface facing away from the absorbent panel;
said diaper further comprises hot melt adhesive strips elongated in the transverse direction and directly coated on the inner surface of said first sheet in said first zones, but not in said second zones; and
said hot melt adhesive strips increase the flexural stiffness of said first sheet in the transverse direction in said first zones compared to said second zones in which said hot melt adhesive strips are not present.

7. The disposable diaper according to claim 6, wherein said hot melt adhesive strips are free of direct contact with the elastic members.

8. The disposable diaper according to claim 1, wherein said first sheet comprises a nonwoven fabric of thermoplastic synthetic fibers;
said first zones comprising spots of locally melt and solidified said nonwoven fabric;
said second zones being free of said spots; and
said spots increase the flexural stiffness of said first sheet in the transverse direction in said first zones compared to said second zones in which said spots are not present.

9. The disposable diaper according to claim 8, wherein said spots of the first zones are free of direct contact with the elastic members.

10. The disposable diaper according to claim 1, wherein
said first zones comprise corrugations of said first sheet;
said corrugations comprise ridges and grooves which are alternatingly arranged in said longitudinal direction and elongated in the transverse direction; and
said corrugations increase the flexural stiffness of said first sheet in the transverse direction in said first zones compared to said second zones in which said corrugations are not present.

11. The disposable diaper according to claim 10, wherein said corrugations of the first zones are free of direct contact with the elastic members.

12. The disposable diaper according to claim 1, wherein said first zones comprise multiple folded layers of said first sheet, said layers being placed one upon another and bonded together; and
said folded layers increase the flexural stiffness of said first sheet in the transverse direction in said first zones compared to said second zones in which said folded layers are not present.

13. The disposable diaper according to claim 1, wherein said first zones of the first sheet are free of the elastic members.

14. The disposable diaper according to claim 1, wherein
the outer and inner ends of the first zones do not extend up to transversely opposite side edges of the chassis and the transversely opposite side edges of the through-hole, respectively.

15. The disposable diaper according to claim 1, wherein said first sheet is liquid-pervious.

16. The disposable diaper according to claim 15, further comprising sheet strips elongated in the transverse direction and bonded to said first sheet in the first zones, said sheet strips increasing the flexural stiffness of said first sheet in the transverse direction in said first zones compared to said second zones in which said sheet strips are not present.

17. The disposable diaper according to claim 15, wherein said diaper further comprises hot melt adhesive strips elongated in the transverse direction and directly coated on said first sheet in said first zones, but not in said second zones; and
said hot melt adhesive strips increase the flexural stiffness of said first sheet in the transverse direction in said first zones compared to said second zones in which said hot melt adhesive strips are not present.

18. The disposable diaper according to claim 15, wherein said first sheet comprises a nonwoven fabric of thermoplastic synthetic fibers;
said first zones comprising spots of locally melt and solidified said nonwoven fabric;
said second zones being free of said spots; and
said spots increase the flexural stiffness of said first sheet in the transverse direction in said first zones compared to said second zones in which said spots are not present.

19. The disposable diaper according to claim 15, wherein said first zones comprise corrugations of said first sheet;

said corrugations comprise ridges and grooves which are alternatingly arranged in said longitudinal direction and elongated in the transverse direction; and said corrugations increase the flexural stiffness of said first sheet in the transverse direction in said first zones compared to said second zones in which said corrugations are not present.

20. The disposable diaper according to claim 15, wherein said first zones comprise multiple folded layers of said first sheet, said layers being placed one upon another and bonded together;

said folded layers increase the flexural stiffness of said first sheet in the transverse direction in said first zones compared to said second zones in which said folded layers are not present; and said first sheet is folded along folding lines to define the folded layers, the folding lines being elongated in the transverse direction.

21. The disposable diaper according to claim 1, wherein the through-hole further includes front and rear edges connecting to the transversely opposite side edges, respectively, and said front and rear edges are free of the elastic members.

* * * * *